United States Patent [19]

Dunlop

[11] 4,219,485
[45] Aug. 26, 1980

[54] BIS(HYDROXYMETHYLFURFURYL)-BUTYLAMINE AND METHOD OF PREPARATION

[75] Inventor: Andrew P. Dunlop, Riverside, Ill.

[73] Assignee: The Quaker Oats Company, Chicago, Ill.

[21] Appl. No.: 62,310

[22] Filed: Jul. 31, 1979

[51] Int. Cl.² ............................................. C07D 307/52
[52] U.S. Cl. .................................... 260/347.7; 528/73
[58] Field of Search ....................................... 260/347.7

[56] References Cited

U.S. PATENT DOCUMENTS

| | | | |
|---|---|---|---|
| 2,995,582 | 8/1961 | Garber et al. | 260/347.7 |
| 4,124,604 | 11/1978 | Yu | 260/347.7 |
| 4,162,327 | 7/1979 | Knoll | 260/347.7 X |

*Primary Examiner*—Richard Raymond
*Attorney, Agent, or Firm*—Neuman, Williams, Anderson & Olson

[57] ABSTRACT

The new composition of matter, bis(hydroxymethylfurfuryl)butylamine.

2 Claims, No Drawings

BIS(HYDROXYMETHYLFURFURYL)BUTYLAMINE AND METHOD OF PREPARATION

This invention relates to a new composition of matter.

The new composition of matter of this invention is bis(hydroxymethylfurfuryl) butylamine having the formula:

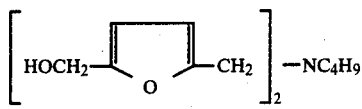

The above new composition of matter is readily produced in substantially quantitative yields at relatively low temperatures by admixing n-butylamine with formaldehyde in aqueous acid solution and adding thereto furfuryl alcohol. The reaction is exothermic in nature and the reaction is conducted without deliberate heating. The resulting solution contains the product bis(hydroxymethylfurfuryl) butylamine which precipitates from solution upon neutralization with a base such as sodium hydroxide.

The following example illustrates a preferred synthesis of the new composition of matter.

EXAMPLE 16.2 grams of formalin (0.2 mole $CH_2O$) containing 10 grams of concentrated hydrochloric acid in 20 milliliters of water and 7.3 grams (0.1 mole) of n-butylamine are mixed. Then 19.6 grams (0.2 mole) of furfuryl alcohol are added dropwise over a period of approximately ½ hour. After addition of all of the furfuryl alcohol the mixture is stirred an additional 1½ hours while being maintained at a temperature of approximately 45° C. Approximately 4.0 grams (0.1 mole) of sodium hydroxide in 15 milliliters of water is added to the reaction mixture with stirring causing a separation of an organic and aqueous layer. One hundred milliliters of tetrahydrofuran is then added and the organic and aqueous layers separated. The separated aqueous layer is washed with tetrahydrofuran and the wash solvent combined with the previously separated organic layer. The combined organic extracts are dried over magnesium sulfate, filtered and evaporated.

The product, bis(hydroxymethylfurfuryl)butylamine, isolated by preparative scale gel permeation chromatography using tetrahydrofuran as solvent, was subjected to infrared (IR) and nuclear magnetic resonance (NMR) analyses which confirmed its structure. The proton (chloroform d) NMR analysis of the compound shows multiple peaks at $\delta 0.87$, $\delta 1.35$ and $\delta 2.42$; single peaks at $\delta 3.60$, $\delta 4.52$ and $\delta 3.60$ ppm.

The infrared spectrum contained a very broad OH stretch band centered at 3340 $cm^{-1}$, very weak furan ring CH stretch vibrations at 3120 $cm^{-1}$, strong $CH_2$ and $CH_3$ stretch vibrations at 2800–2960 $cm^{-1}$, medium furan ring C=C stretch at 1555 $cm^{-1}$ and 1425–1470 $cm^{-1}$, strong ether CO band at 1012 $cm^{-1}$ and a strong HC=CH wag vibration at 790 $cm^{-1}$.

The bis(hydroxymethylfurfuryl)butylamine composition of the present invention is useful in the fabrication of polyurethane compositions containing a substantial furan ring-portion thereof. Reaction of the composition of the present invention with a polyisocyanate results in the formation of a polyurethane. The composition of the invention provides not only a diol for reaction with the polyisocyanate, but also provides a tertiary amine catalyst component which becomes incorporated into the resulting urethane structure.

Those modifications and equivalents which fall within the spirit of the invention are to be considered a part thereof.

What is claimed is:

1. As a new composition of matter, bis(hydroxymethylfurfuryl)butylamine.

2. A process for preparing bis(hydroxymethylfurfuryl)butylamine which comprises admixing n-butylamine with formaldehyde in aqueous acid solution and adding to the mixture furfuryl alcohol at a temperature not above about 45° C.

* * * * *